United States Patent
Moriwaki et al.

(10) Patent No.: US 11,925,492 B2
(45) Date of Patent: Mar. 12, 2024

(54) IMAGE PROCESSING APPARATUS AND IMAGE PROCESSING METHOD

(71) Applicant: FUJITSU LIMITED, Kawasaki (JP)

(72) Inventors: Yasutaka Moriwaki, Kawasaki (JP); Hiroaki Takebe, Kawasaki (JP); Nobuhiro Miyazaki, Kawasaki (JP); Takayuki Baba, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 90 days.

(21) Appl. No.: 17/166,819

(22) Filed: Feb. 3, 2021

(65) Prior Publication Data

US 2021/0287369 A1    Sep. 16, 2021

(30) Foreign Application Priority Data

Mar. 16, 2020  (JP) .................................. 2020-45198

(51) Int. Cl.
*G06T 7/00* (2017.01)
*A61B 6/03* (2006.01)
(Continued)

(52) U.S. Cl.
CPC ............ *A61B 6/032* (2013.01); *G06T 7/0014* (2013.01); *G06V 10/30* (2022.01); *G06V 10/507* (2022.01);
(Continued)

(58) Field of Classification Search
CPC ......... G06T 7/0014; G06T 2207/10081; G06T 2207/30061; G06T 2207/20081;
(Continued)

(56) References Cited

U.S. PATENT DOCUMENTS

2003/0223627 A1   12/2003  Hiroyuki et al.
2013/0223687 A1*  8/2013  Kimoto .................. A61B 6/032
                                                                 382/103
(Continued)

FOREIGN PATENT DOCUMENTS

JP   H08-320923 A   12/1996
JP   2008-253293 A  10/2008
(Continued)

OTHER PUBLICATIONS

Liu, Caixi, et al., "A fully automatic segmentation algorithm for CT lung images based on random forest", Medical Physics, Dec. 29, pp. 518-529, vol. 47, No. 2, US (2019).
(Continued)

*Primary Examiner* — Wesley J Tucker
*Assistant Examiner* — Han Hoang
(74) *Attorney, Agent, or Firm* — ArentFox Schiff LLP

(57) ABSTRACT

A non-transitory computer-readable recording medium having stored an image processing program that causes a computer to execute a process, the process includes extracting a plurality of consecutive pixels corresponding to a first part or a second part of a body, from a pixel column in a predetermined direction of an image of the body, obtaining
(Continued)

a statistical value of pixel values of the plurality of consecutive pixels, and identifying a part corresponding to the plurality of consecutive pixels, among the first part or the second part, based on the statistical value.

6 Claims, 12 Drawing Sheets

(51) Int. Cl.
    *G06V 10/30*     (2022.01)
    *G06V 10/50*     (2022.01)

(52) U.S. Cl.
    CPC ............... *G06T 2207/10081* (2013.01); *G06T 2207/30061* (2013.01)

(58) Field of Classification Search
    CPC ........... G06T 7/11; G06T 7/136; G06T 7/174; G06V 10/751; G06V 10/30; G06V 10/507; G06V 2201/031; A61B 6/5217; A61B 6/5223; A61B 6/032
    See application file for complete search history.

(56) References Cited

U.S. PATENT DOCUMENTS

| | | |
|---|---|---|
| 2015/0279086 A1 | 10/2015 | Ogino et al. |
| 2019/0197688 A1 | 6/2019 | Moriwaki et al. |
| 2019/0385015 A1* | 12/2019 | Miyajima ................. G06T 7/11 |
| 2019/0392584 A1* | 12/2019 | Song .......................... G06T 7/11 |
| 2020/0120236 A1* | 4/2020 | Miyashita ................. G06T 7/12 |

FOREIGN PATENT DOCUMENTS

| | | |
|---|---|---|
| JP | 2016-182454 A | 10/2016 |
| JP | 2018-151791 A | 9/2018 |

OTHER PUBLICATIONS

Beigeman-Aubry, Catherine, et al., "Multi-Detector Row CT and Postprocessing Techniques in the Assessment of Diffuse Lung Disease", RADIOGRAPHICS, pp. 1639-1652, vol. 25, No. 6, US (Nov. 1, 2005).

Extended European Search Report issued by the European Patent Office corresponding to European Patent Application No. 21153276.7-1207 (dated Jul. 19, 2021).

"Development of AI-Based Technology to Retrieve Similar Disease Cases in CT Inspections", Press release by FUJITSU Laboratories Ltd., URL: http://pr.fujitsu.com/jp/news/2017/06/23.html, Jun. 23, 2017.

"Organs", Health Terms WEB Encyclopedia, URL: https://health.joyplot.com/HealthWordsWiki/?%E8%87%93%E5%99%A8, as viewed on Feb. 26, 2020.

"2014 Radiologists Question & Answer Explanation [Basic 1-5]", URL: https://xn--o1gq22cilllou16giui.jp/archives/21373, as viewed Jan. 29, 2015.

Office Action of European Patent Application No. 21153276.7 dated Feb. 15, 2023.

* cited by examiner

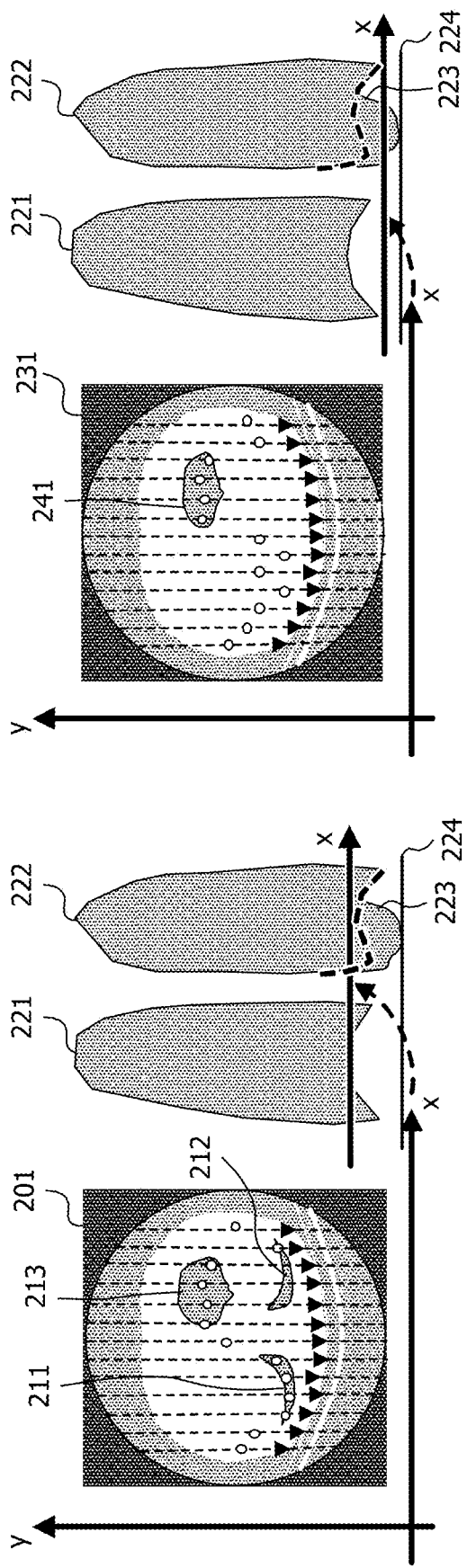

IMAGE PROCESSING APPARATUS AND IMAGE PROCESSING METHOD

CROSS-REFERENCE TO RELATED APPLICATION

This application is based upon and claims the benefit of priority of the prior Japanese Patent Application No. 2020-45198, filed on Mar. 16, 2020, the entire contents of which are incorporated herein by reference.

FIELD

The embodiments discussed herein are related to image processing.

BACKGROUND

In diagnostic imaging for diagnosing cases using a computed tomography (CT) image, it is said to be difficult to diagnose cases in which lesions are distributed in a plurality of regions over a wide range, such as diffuse pulmonary disease. When diagnosing such cases, doctors narrow down candidates for disease names by referring to similar cases for which a definite diagnose has been made in the past.

However, searching for past similar cases takes time, which is a large burden on the doctor. Therefore, a similar case image search technique has been proposed which automatically searches for CT images of similar cases from the past cases and presents a search result to support a diagnosis task of the doctor (for example, refer to Japanese Laid-open Patent Publication No. 2018-151791 and "Development of AI-Based Technology to Retrieve Similar Disease Cases in CT Inspections", [online], Jun. 23, 2017, Press release by Fujitsu Laboratories Ltd., [searched on Jan. 8, 2020], Internet <URL: http://prfujitsu.com/jp/news/2017/06/23.html>). The pixel values of the CT image may be referred to as CT values.

In this similar case image search technique, an organ region extracted from a medical image is divided into a plurality of regions, and the number of pixels indicating a lesion in each of the plurality of regions is counted. With reference to a storage unit that stores the number of pixels indicating the lesion for each region, a similar case image corresponding to a similarity of the number of pixels indicating the lesion is specified.

In relation to CT images, classification of solid organs and hollow organs is also known (for example, refer to "Organs", [online], Health Terms WEB Encyclopedia, [searched on Feb. 26, 2020], Internet <URL: https://health.joyplot.com/HealthWordsWiki/?%E8%87%93% E5%99% A8>). The CT value of each organ is also known (for example, refer to "2014 Radiologists Question & Answer Explanation [Basic 1-5]", [online], Jan. 29, 2015, Image Diagnosis Summary, [search on Feb. 26, 2020], Internet <URL: https://xn--o1qq22cjlllou16giuj.jp/archives/21373>). A diagnostic image generation apparatus that generates a three-dimensional projection image from medical volume data by rendering, and a lung field region extraction method that extracts the entire lung field region including a lost lung field region from the CT image are also known (for example, refer to Japanese Laid-open Patent Publication No. 2016-182454 and Japanese Laid-open Patent Publication No. 2008-253293).

SUMMARY

According to an aspect of the embodiments, a non-transitory computer-readable recording medium having stored an image processing program that causes a computer to execute a process, the process includes extracting a plurality of consecutive pixels corresponding to a first part or a second part of a body, from a pixel column in a predetermined direction of an image of the body, obtaining a statistical value of pixel values of the plurality of consecutive pixels, and identifying a part corresponding to the plurality of consecutive pixels, among the first part or the second part, based on the statistical value.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 2A and 2B are diagrams illustrating a CT image from which it is difficult to generate an accurate coronal image;

DESCRIPTION OF EMBODIMENTS

Figure 1A:
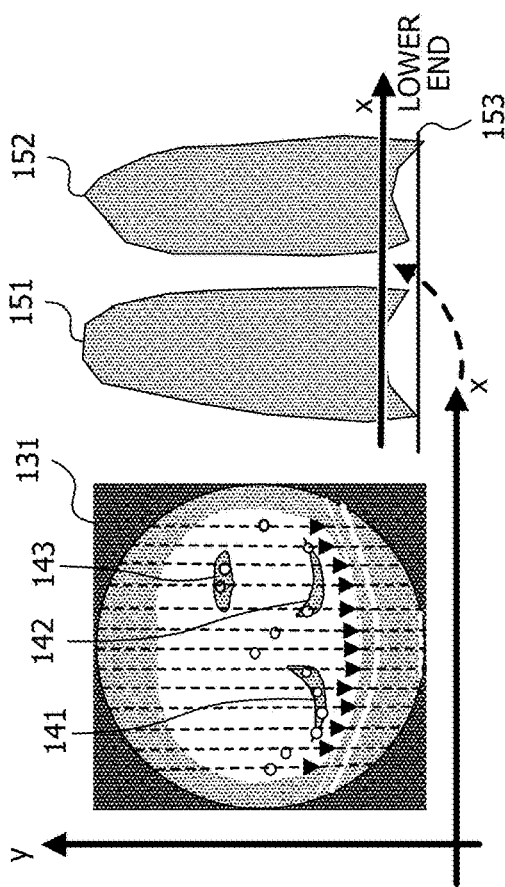
FIGS. 1A and 1B are diagrams illustrating a CT image from which an accurate coronal image may be generated.

According to the similar case image search technique in the related art, feature amounts are extracted from a CT image of each of a plurality of slices of a lung field, a result obtained by combining the extracted feature amounts is quantified as a three-dimensional distribution of a lesion, and thereby cases having similar distributions may be searched for. At this time, in order to take into consideration individual differences in the size of the lung field, the positions of the upper end and the lower end of the lung field are calculated, and feature amount extraction is performed on a predetermined number of CT images which are extracted from the plurality of CT images from the upper end to the lower end.

Therefore, in a case where the calculation results of the upper end and the lower end of the lung field largely deviate from the original correct positions, it is difficult to accurately calculate the three-dimensional distribution of the lesion. Therefore, the calculation accuracy of the upper end and the lower end of the lung field greatly affects the calculation accuracy of the three-dimensional distribution of the lesion in the lung field.

For example, the positions of the upper end and the lower end of the lung field may be calculated by generating a coronal image indicating a sectional shape of the lung field from the CT images of the plurality of slices of the body. However, in a case where a lung field region and a region of an organ other than the lung field are mixed in the CT image, it is difficult to generate a coronal image indicating an accurate sectional shape of the lung field. In this case, it is desirable to generate a coronal image by extracting only the lung field region from the CT image.

Such a problem occurs in a case where a plurality of different body parts are mixed in the CT image as well as in the case of generating a coronal image indicating the sectional shape of the lung field. Such a problem occurs in various images including body parts of a human or animal as well as in the CT image of a human body.

Hereinafter, embodiments of a technique for distinguishing a plurality of parts included in an image of a body will be described in detail with reference to the drawings.

In the CT image of the slice of the lung field, there may be a region corresponding to a hollow portion of an organ other than the lung field, such as a stomach or a large intestine in addition to the lung field region. As described in "Organs", [online], Health Terms WEB Encyclopedia, [searched on Feb. 26, 2020], Internet <URL: https://health.joyplot.com/HealthWordsWiki/?%E8%87%93% E5%99%A8>, the lung field is a solid organ formed by closely binding cells having a function, and the stomach and the large intestine are tubular hollow organs through which substances such as ingested food pass.

As described in "2014 Radiologists Question & Answer Explanation [Basic 1-5]", [online], Jan. 29, 2015, Image Diagnosis Summary, [search on Feb. 26, 2020], Internet <URL: https://xn--o1qq22cjlllou16giuj.jp/archives/21373>, the CT value represents a percentage of attenuation of X-rays when the X-rays pass through a human body, and the CT value of air is defined as −1000 HU. Since the content of the hollow organ such as the stomach or the large intestine is a cavity (air), the CT value of the hollow organ is approximately −1000 HU. On the other hand, since the lung field is a solid organ and the content thereof is not completely hollow, the CT value of the lung field is a value larger than −1000 HU. The CT values of other parts such as bones, muscles, blood vessels, and fat are values much larger than the CT value of the lung field.

In the CT image of the slice of the lung field, the coordinate in the left-right direction of the body is defined as an x coordinate, and the coordinate in the front-rear direction of the body is defined as a y coordinate. In a case where a CT image does not satisfy any of the following conditions a and b, or in a case where a CT image satisfies only the condition a, an accurate coronal image of the lung field may be generated from the CT image of each of a plurality of slices by using the features of the CT values of the lung field.

Condition a: a lung field region and a region W corresponding to a hollow portion of a hollow organ are present in the CT image, and the range of the x coordinate of the region W overlaps the range of the x coordinate of the lung field region.

Condition b: when CT images are sequentially selected from the upper lung field toward the lower lung field, the region W is continuously included even in the CT image which no longer includes the lung field region.

Figure 1B:
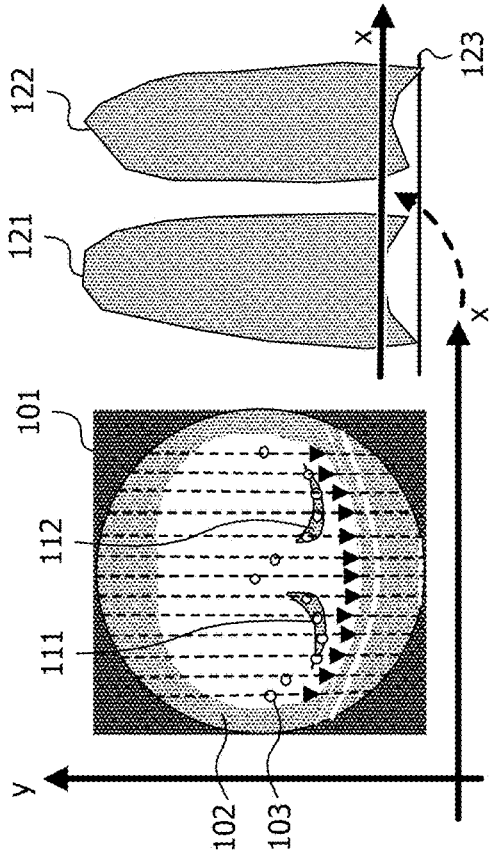

FIGS. 1A and 1B are diagrams illustrating an example of a CT image from which an accurate coronal image may be generated. FIG. 1A illustrates an example of a CT image 101 that satisfies neither condition a nor condition b. The x coordinate represents a coordinate in the left-right direction of the body, and the y coordinate represents a coordinate in the front-rear direction of the body. A circular region 102 represents the field of view (FOV) of the CT apparatus that generates the CT image. In the circular region 102, broken lines parallel to the y axis represent a plurality of pixels having the same x coordinate.

In the CT image 101 of the slice of the lower lung field, a lung field region 111 of the left lung and a lung field region 112 of the right lung are included, and a region of a hollow portion of a hollow organ is not included. In this case, a computer obtains a minimum value 103 of the CT values of the plurality of pixels having the same x coordinate at each position on the x axis indicated by the broken line, and plots the minimum value 103 at the corresponding position on the plane of the coronal image. Since the region of the hollow portion of the hollow organ is not included, in the range of the x coordinates of the lung field region 111 or the lung field region 112, the minimum value 103 represents the CT value of the lung field region 111 or the lung field region 112.

The computer repeats the same processing for the CT image of each of the plurality of slices to generate a coronal image including a lung field region 121 of the left lung and a lung field region 122 of the right lung. The computer analyzes the coronal image to calculate the position of a lower end 123 of the lung field.

FIG. 1B illustrates an example of a CT image 131 that satisfies the condition a and does not satisfy the condition b. In the CT image 131 of the slice of the lower lung field, a region 143 of the hollow portion of the hollow organ is included in addition to a lung field region 141 of the left lung and a lung field region 142 of the right lung, and the range of the x coordinate of the region 143 overlaps the range of the x coordinate of the lung field region 142. However, when CT images are sequentially selected from the upper lung field toward the lower lung field, the region of the hollow portion of the hollow organ is also not included in the CT image which no longer includes the lung field region.

In this case, the computer repeats the same processing as in the case of FIG. 1A to generate a coronal image including a lung field region 151 of the left lung and a lung field region 152 of the right lung. In the range of the x coordinate of the region 143, the minimum value of the CT values represents the CT value of the region 143, not the lung field region 142. However, since the CT value of the region 143 are similar to the CT value of the lung field region 142, the shape of the lung field region 152 included in the coronal image is not greatly affected. The computer analyzes the coronal image to calculate the position of a lower end 153 of the lung field.

FIGS. 2A and 2B illustrate an example of a CT image from which it is difficult to generate an accurate coronal image because both of the condition a and the condition b are satisfied. FIG. 2A illustrates an example of a CT image 201 including a lung field region and a region corresponding to a hollow portion of a hollow organ. In the CT image 201 of the slice of the lower lung field, a region 213 of the hollow portion of the hollow organ is included in addition to a lung field region 211 of the left lung and a lung field region 212 of the right lung, and the range of the x coordinate of the region 213 overlaps the range of the x coordinate of the lung field region 212. In this case, in the range of the x coordinate of the region 213, the minimum value of the CT values represents the CT value of the region 213, not the lung field region 212.

FIG. 2B illustrates an example of a CT image 231 which includes a region corresponding to a hollow portion of a hollow organ and does not include a lung field region. The CT image 231 is a CT image of a slice further below the CT image 201. In the CT image 231, a region 241 of the hollow portion of the hollow organ is included, and a lung field region is not included. In this case, in the range of the x coordinate of the region 241, the minimum value of the CT values represents the CT value of the region 241.

The computer repeats the same processing as in the case of FIGS. 1A and 1B to generate a coronal image including a lung field region 221 of the left lung and a lung field region 222 of the right lung. However, when CT images are sequentially selected from the upper lung field toward the lower lung field, the region 241 of the hollow portion of the hollow organ is continuously included even in the CT image 231 which no longer includes the lung field region. Therefore, the shape of the lung field region 222 includes a projection 223 corresponding to the shape of the hollow organ, and the position of a lower end 224 of the lung field calculated from the coronal image is lower than the actual lower end.

Figure 3:
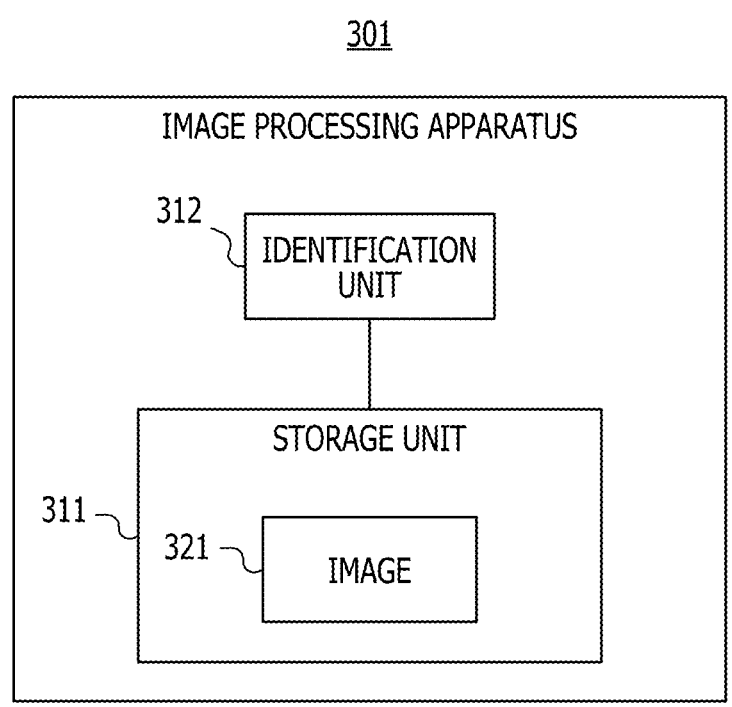
FIG. 3 is a functional configuration diagram of an image processing apparatus.

FIG. 3 illustrates an example of a functional configuration of an image processing apparatus according to the embodiment. An image processing apparatus 301 in FIG. 3 includes a storage unit 311 and an identification unit 312. The storage unit 311 stores an image 321 of the body. The identification unit 312 performs image processing on the image 321.

Figure 4:
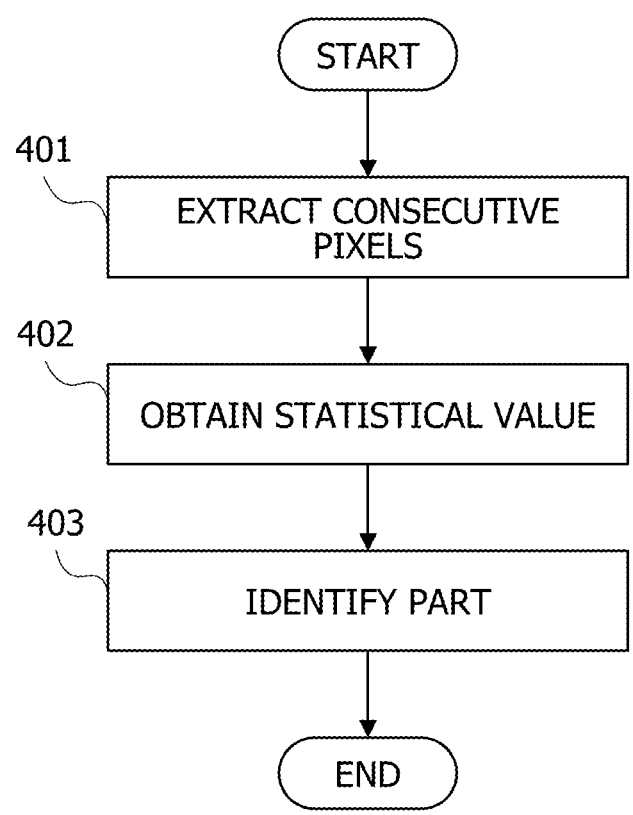
FIG. 4 is a flowchart of image processing.

FIG. 4 is a flowchart illustrating an example of image processing performed by the image processing apparatus 301 in FIG. 3. First, the identification unit 312 extracts a plurality of consecutive pixels corresponding to a first part or a second part of the body from a pixel column in a predetermined direction of the image 321 (operation 401), and obtains a statistical value of pixel values of the plurality of consecutive pixels (operation 402). The identification unit 312 identifies a part corresponding to the plurality of consecutive pixels, among the first part or the second part based on the statistical value (operation 403).

With the image processing apparatus 301 in FIG. 3, a plurality of parts included in the image of the body may be distinguished.

Figure 5:
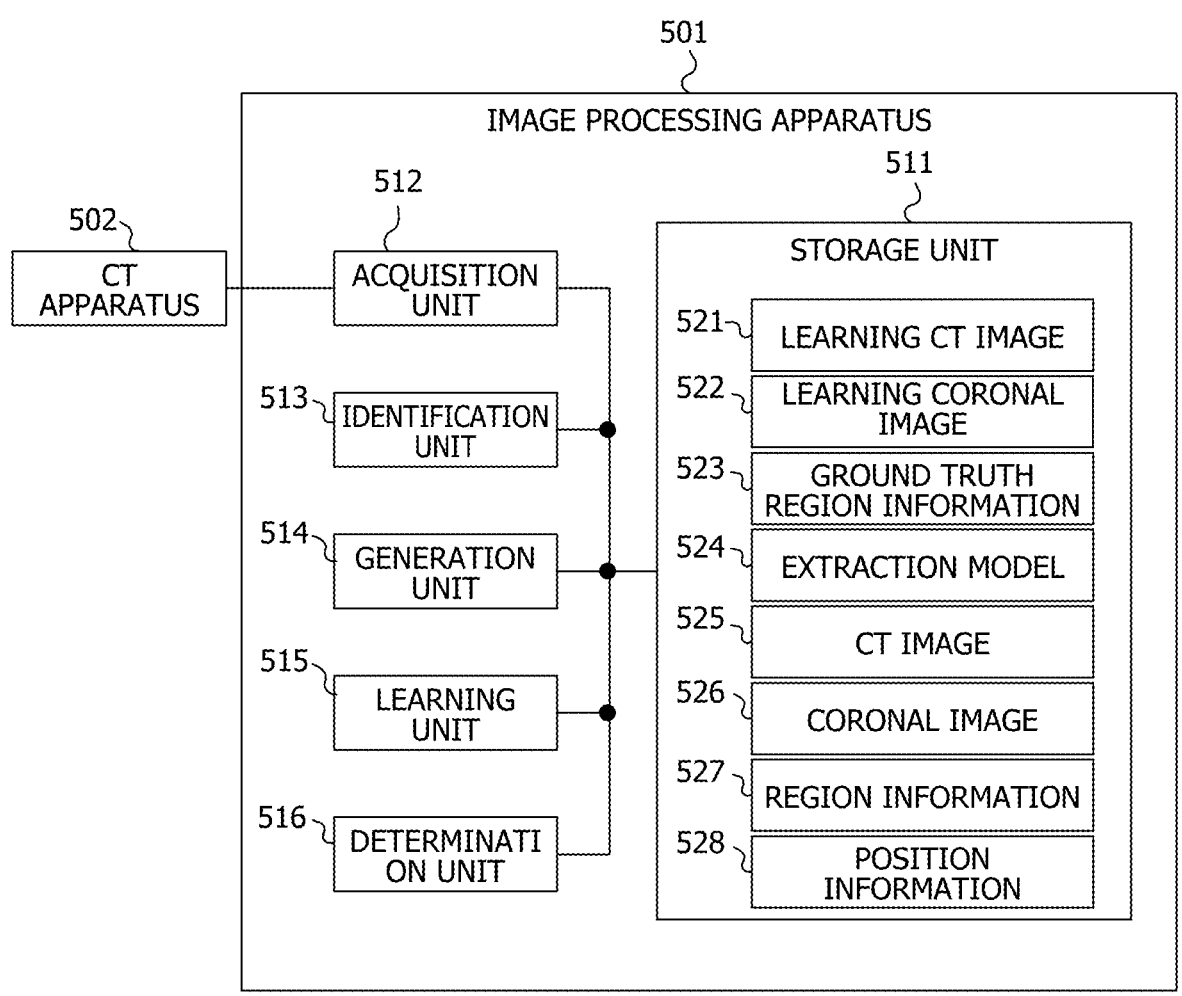
FIG. 5 is a functional configuration diagram illustrating a specific example of the image processing apparatus.

FIG. 5 illustrates a specific example of the image processing apparatus 301 in FIG. 3. An image processing apparatus 501 in FIG. 5 includes a storage unit 511, an acquisition unit 512, an identification unit 513, a generation unit 514, a learning unit 515, and a determination unit 516. The storage unit 511 and the identification unit 513 correspond to the storage unit 311 and the identification unit 312 in FIG. 3, respectively.

A CT apparatus 502 is installed in a medical institution, and captures a CT image of a patient. The image processing apparatus 501 and the CT apparatus 502 may communicate with each other via a communication network.

Figure 6:
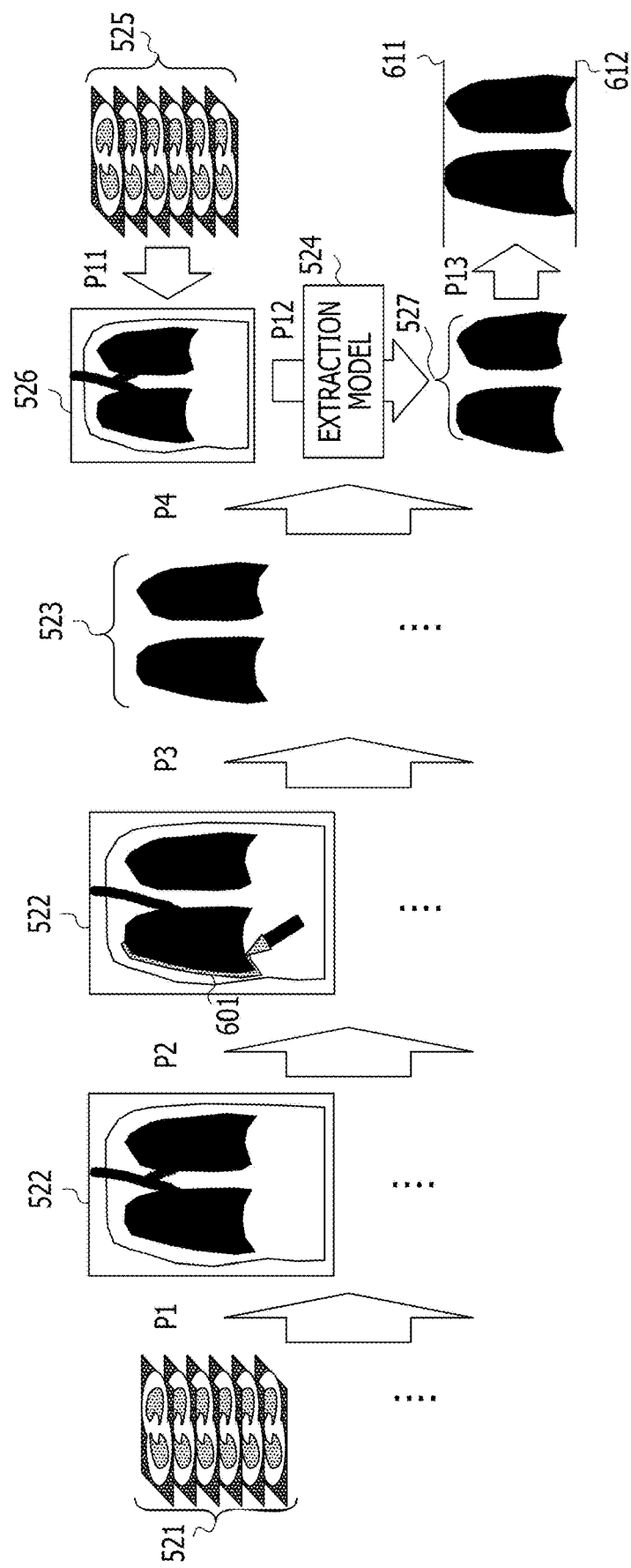
FIG. 6 is a diagram illustrating image processing.

FIG. 6 illustrates an example of image processing performed by the image processing apparatus 501 in FIG. 5. The image processing apparatus 501 has two operation modes which are a learning mode and an operation mode. In the learning mode, the image processing apparatus 501 generates an extraction model 524 for extracting a lung field region from a coronal image in the following procedures, for example.

P1: The acquisition unit 512 acquires a learning CT image 521 of each of a plurality of patients from the CT apparatus 502, and stores the learning CT image in the storage unit 511. The learning CT image 521 is a CT image of a slice of a body including a lung field, and a plurality of learning CT images 521 corresponding to a plurality of slices are acquired for each patient. The identification unit 513 identifies a lung field region corresponding to the lung field in each learning CT image 521. The generation unit 514 generates a learning coronal image 522 indicating the sectional shape of the lung field, from the lung field region of each of the plurality of learning CT images 521 of each patient, and stores the learning coronal image in the storage unit 511.

P2: The user adds an annotation 601 indicating the lung field region, to the learning coronal image 522 of each patient.

P3: The generation unit 514 generates ground truth region information 523 indicating the lung field region in the learning coronal image 522, based on the annotation 601 added to the learning coronal image 522, and stores the ground truth region information in the storage unit 511.

P4: The learning unit 515 causes the learning model to learn the learning coronal images 522 and the ground truth region information 523 of the plurality of patients to generate the extraction model 524 that is a trained model, and stores the extraction model in the storage unit 511.

In the operation mode, the image processing apparatus 501 determines the upper end and the lower end of the lung field in the following procedures, for example.

P11: The acquisition unit 512 acquires a plurality of CT images 525 of a patient as a diagnosis target, from the CT apparatus 502, and stores the CT images in the storage unit 511. The CT image 525 is an example of the image 321 in FIG. 3. The identification unit 513 identifies a lung field region in each CT image 525, and the generation unit 514 generates a coronal image 526 of the lung field from the lung field region of each of the plurality of CT images 525 and stores the coronal image in the storage unit 511.

P12: The determination unit 516 extracts a lung field region from the coronal image 526 by using the extraction model 524, generates region information 527 indicating the extracted lung field region, and stores the region information in the storage unit 511.

P13: The determination unit 516 determines an upper end 611 and a lower end 612 of the lung field by analyzing the image of the lung field region indicated by the region information 527, generates position information 528 indicating the upper end 611 and the lower end 612, and stores the position information in the storage unit 511.

Next, the processing of identifying the lung field region in the CT image 525 in procedure P11 will be described. The processing of identifying the lung field region in the learning CT image 521 in procedure P1 is also similar to procedure P11.

The identification unit 513 distinguishes the lung field region from the region W by using the difference between the CT value of the lung field region and the CT value of the region W corresponding to the hollow portion of the hollow organ. The lung field is an example of the first part, and the hollow organ is an example of the second part. The following medical findings are obtained from the description of "2014 Radiologists Question & Answer Explanation [Basic 1-5]", [online], Jan. 29, 2015, Image Diagnosis Summary, [search on Feb. 26, 2020], Internet <URL: https://xn--o1qq22cjlllou16giuj.jp/archives/21373> and the like.

CT value of lung field region: about −1000 HU to about −500 HU CT value of region W: about −1000 HU CT value of soft tissue, bone or the like: about 100 HU to about 1000 HU According to the above-described medical findings, it is assumed that the CT value of the lung field region is greater than the CT value of the region W. However, in a case where the CT values of individual pixels are compared, there is also a possibility that the CT value of the lung field region is smaller than the CT value of the region W incidentally. Therefore, the identification unit 513 obtains the statistical value of the CT values of the plurality of pixels included in a determination target region, and identifies whether the determination target region is the lung field region or the region W based on the statistical value.

In procedure P11, the image processing apparatus 501 identifies a lung field region in the CT image 525, and generates the coronal image 526 of the lung field, from the lung field region of each of the plurality of CT images 525, for example, in the following procedures P21 to P28 (not illustrated).

- P21: The identification unit 513 performs binarization processing on the CT image 525 to extract a contour of each region. As a threshold T1 for the binarization processing, for example, a CT value in a range of −100 HU to 0 HU is used. The identification unit 513 generates a processing target CT image by converting the CT values of pixels belonging to regions other than the region having the largest internal area into predetermined values. As the predetermined value, for example, a CT value equal to or greater than the threshold T1 is used.

Figure 7:
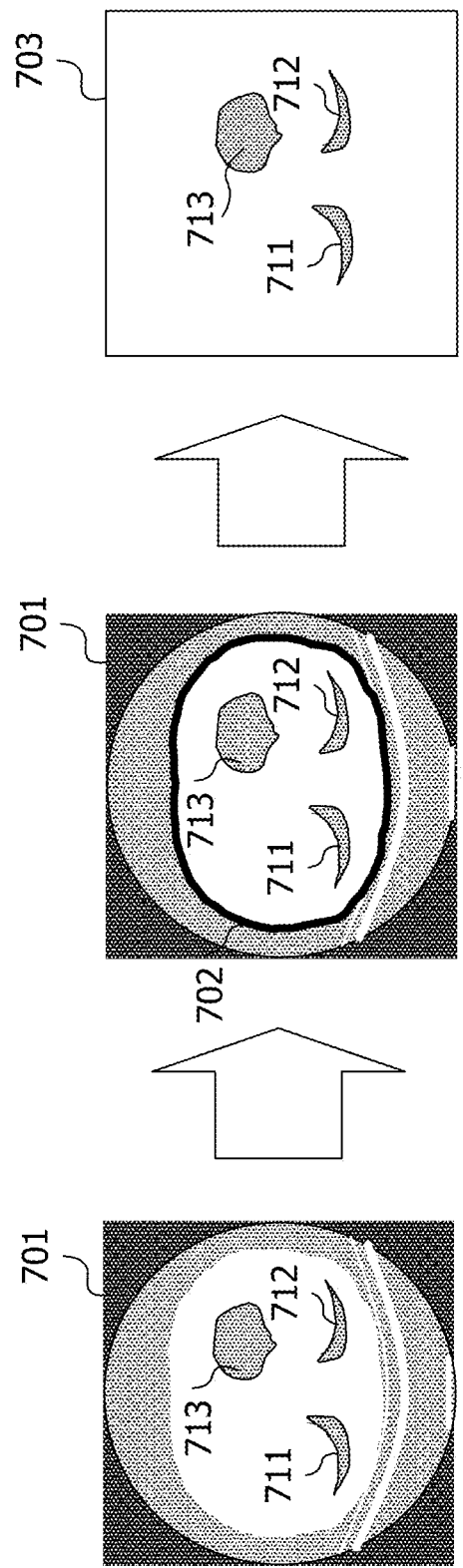
FIG. 7 is a diagram illustrating a processing target CT image.

FIG. 7 illustrates an example of the processing target CT image. A CT image 701 before the conversion includes a lung field region 711 of the left lung, a lung field region 712 of the right lung, and a region 713 of the hollow portion of the hollow organ. By performing the binarization processing on the CT image 701, in addition to contours of the lung field region 711, the lung field region 712, and the region 713, a contour of a body region 702 including these regions is also extracted. Since the body region 702 corresponds to a region having the largest internal area, CT values of pixels belonging to a region outside the body region 702 are converted into predetermined values, and thereby a processing target CT image 703 is generated.

- P22: The identification unit 513 selects one x coordinate of the processing target CT image, and identifies a pixel column in a direction of a straight line parallel to the y axis at the position of the selected x coordinate. The direction of the straight line parallel to the y axis is an example of the predetermined direction.
- P23: The identification unit 513 extracts a partial pixel column corresponding to the lung field region or the region W from the identified pixel column. For example, the identification unit 513 compares the CT value of each pixel included in the pixel column with a threshold T2. The identification unit 513 extracts a plurality of consecutive pixels each of which has a CT value equal to or smaller than the threshold T2, as the partial pixel column corresponding to the lung field region or the region W.

The threshold T2 may be determined based on the above-described medical findings, or may be determined by performing statistical processing on CT values of actual CT images. In the case of using the statistical processing, the threshold T2 that separates a group of CT values of the lung field region and the region W from a group of CT values of the other parts may be determined from a distribution of CT values obtained by collecting the CT values of the lung field region, the region W, and the other parts. As the threshold T2, for example, a CT value in a range of −500 HU to 100 HU is used. The threshold T2 is an example of a second threshold.

By using such a threshold T2, a partial pixel column corresponding to the lung field region or the region W may be accurately extracted.

- P24: For each extracted partial pixel column, the identification unit 513 obtains a statistical value V of the CT values of the plurality of pixels included in the partial pixel column. As the statistical value V, an average value, a median value, a mode value, or the like may be used.
- P25: The identification unit 513 compares the statistical value V with a threshold T3. The threshold T3 is a CT value smaller than the threshold T2. The identification unit 513 determines that the partial pixel column corresponds to the lung field region in a case where the statistical value V is greater than the threshold T3, and determines that the partial pixel column corresponds to the region W in a case where the statistical value V is equal to or smaller than the threshold T3. The identification unit 513 identifies the partial pixel column determined to correspond to the lung field region, as a part of the lung field region.

The threshold T3 may be determined based on the above-described medical findings, or may be determined by performing statistical processing on CT values of actual CT images. In the case of using the statistical processing, the threshold T3 that separates a group of CT values of the lung field region from a group of CT values of the region W may be determined from a distribution of CT values obtained by collecting the CT values of the lung field region and the region W. As the threshold T3, for example, a CT value in a range of −1000 HU to −900 HU is used. The threshold T3 is an example of a first threshold.

By comparing the statistical value V of the CT values of the partial pixel column with the threshold T3, it may be accurately determined whether the partial pixel column corresponds to the lung field region or the region W.

- P26: In a case where one or more partial pixel columns corresponding to the lung field region are extracted from the pixel column, the generation unit 514 selects these partial pixel columns and obtains the minimum value of the CT values of the plurality of pixels included in the selected partial pixel column. The generation unit 514 plots the minimum value at a position corresponding to the slice of the CT image 525 and the x coordinate of the pixel column, in the plane of the coronal image 526.
- P27: The image processing apparatus 501 repeats the processing of procedures P22 to P26 for all of the x coordinates of the processing target CT image.
- P28: The image processing apparatus 501 repeats the processing of procedures P21 to P27 for the CT images 525 corresponding to all of the slices of the patient as the diagnosis target. Thus, the coronal image 526 of the patient as the diagnosis target is generated.

With such image processing, the pixels of the lung field region and the pixels of the region W in the CT image 525 are distinguished from each other, and the coronal image 526 is generated using only the CT values of the lung field region. Thus, since the CT values of the region W are computationally ignored, the accurate coronal image 526 may be generated by excluding the influence of the region W. By using the accurate coronal image 526, the accurate positions of the upper end and the lower end of the lung field may be obtained.

In the case of simply distinguishing the lung field region from the region W in the CT image 525 without generating the coronal image 526, any direction in the CT image 525 may be used as the predetermined direction in procedure P22. In this case, the predetermined direction may be a direction parallel to the x axis, or may be a direction intersecting the x axis at a predetermined angle.

Figure 8:
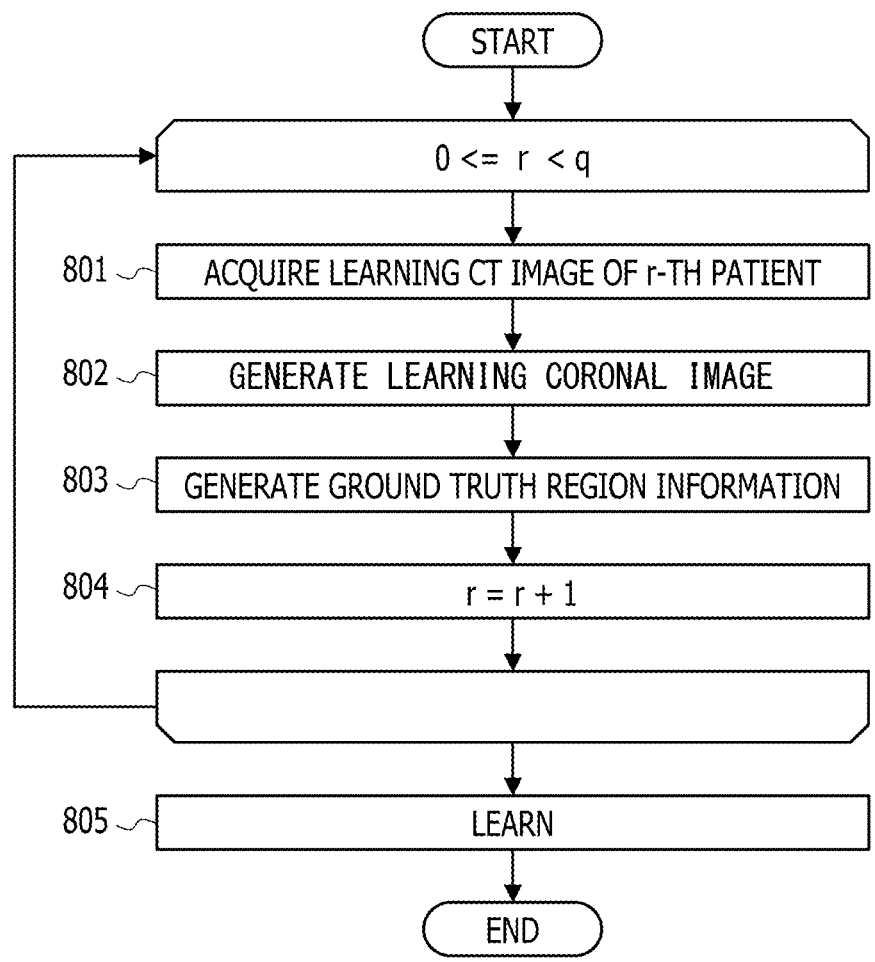
FIG. 8 is a flowchart of image processing in a learning mode.

FIG. 8 is a flowchart illustrating an example of image processing in a learning mode performed by the image processing apparatus 501 in FIG. 5. First, the image processing apparatus 501 sets 0 for a control variable r indicating any of q (q is an integer of 2 or more) patients. The acquisition unit 512 acquires n (n is an integer of 2 or more) learning CT images 521 of the r-th patient, from the CT apparatus 502 (operation 801).

Next, the image processing apparatus 501 generates the learning coronal image 522 of the lung field, from the lung field region of each of the n learning CT images 521 (operation 802). The user adds an annotation to the learning coronal image 522, and the generation unit 514 generates ground truth region information 523 indicating the lung field region in the learning coronal image 522 based on the added annotation (operation 803).

Next, the image processing apparatus 501 increments r by 1 (operation 804), and in a case where r<q, the image processing apparatus 501 repeats the processing of operation 801 to operation 804.

In a case where r reaches q in operation 804, the learning unit 515 causes the learning model to learn the learning coronal image 522 and the ground truth region information 523 of the 0-th to q−1-th patients to generate the extraction model 524 (operation 805).

Figure 9:
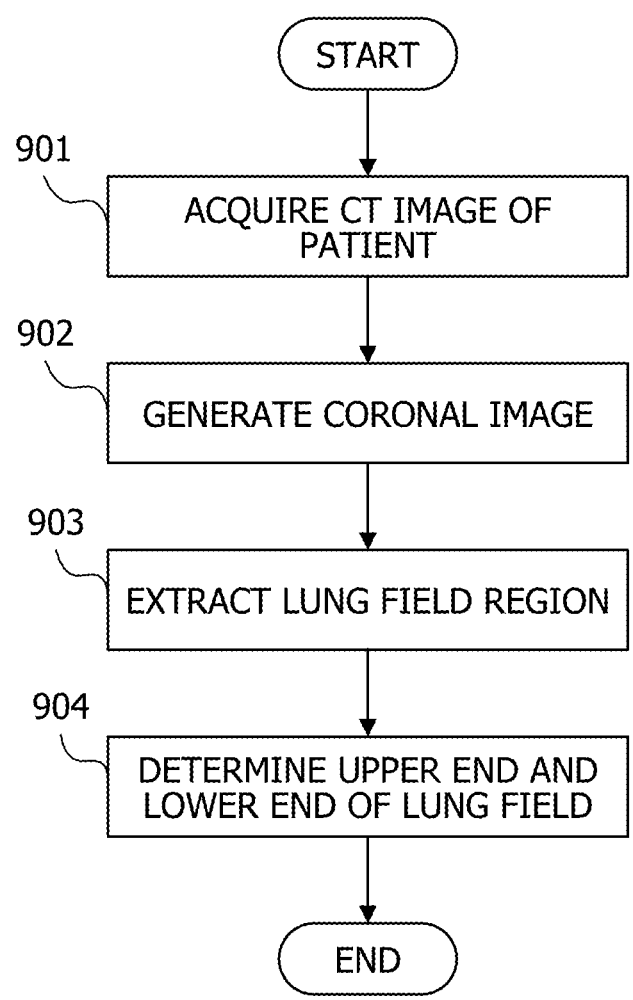
FIG. 9 is a flowchart of image processing in an operation mode.

FIG. 9 is a flowchart illustrating an example of image processing in an operation mode performed by the image processing apparatus 501 in FIG. 5. First, the acquisition unit 512 acquires n CT images 525 of the patient as the diagnosis target, from the CT apparatus 502 (operation 901). The image processing apparatus 501 generates the coronal image 526 of the lung field, from the lung field region of each of the n CT images 525 (operation 902).

Next, the determination unit 516 extracts the lung field region from the coronal image 526 by using the extraction model 524, and generates the region information 527 indicating the extracted lung field region (operation 903). The determination unit 516 determines the upper end and the lower end of the lung field by using the region information 527, and generates the position information 528 indicating the upper end and the lower end (operation 904).

Figure 10:
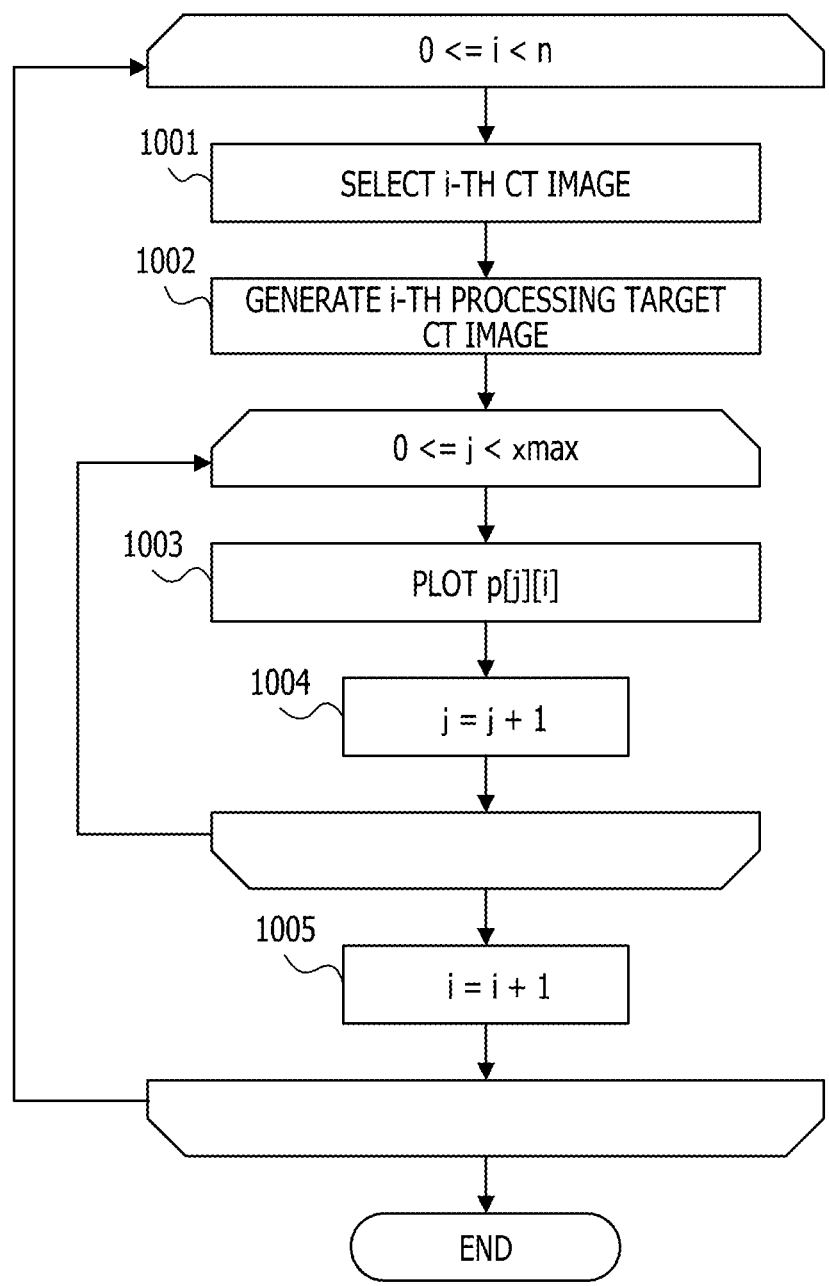
FIG. 10 is a flowchart of coronal image generation processing.

FIG. 10 is a flowchart illustrating an example of coronal image generation processing in operation 902 in FIG. 9. The coronal image generation processing in operation 802 in FIG. 8 is the same as the coronal image generation processing in FIG. 10.

First, the image processing apparatus 501 sets 0 for a control variable i indicating any of the n CT images 525. The identification unit 513 selects the i-th CT image 525 (operation 1001), performs binarization processing on the selected CT image 525, and generates the i-th processing target CT image (operation 1002).

The position (x,y) of the pixel in the processing target CT image is described by using xmax (xmax is an integer of 2 or more) x coordinates and ymax (ymax is an integer of 2 or more) y coordinates. In this case, xmax represents the width of the processing target CT image, and ymax represents the height of the processing target CT image.

On the other hand, the position (x,y) of the pixel in the coronal image 526 is described by using xmax x coordinates and n y coordinates. As the x coordinate of the coronal image 526, the same x coordinate as that of the processing target CT image is used. The y coordinate of the coronal image 526 corresponds to any slice of the n CT images 525. In this case, xmax represents the width of the coronal image 526, and n represents the height of the coronal image 526.

Next, the image processing apparatus 501 sets 0 for a control variable j indicating an x coordinate of the coronal image 526. The generation unit 514 obtains a pixel value p[j][i] of the pixel at the position (j,i) in the coronal image 526, and plots p[j][i] on the plane of the coronal image 526 (operation 1003).

Next, the image processing apparatus 501 increments j by 1 (operation 1004), and in a case where j<xmax, the image processing apparatus 501 repeats the processing of operation 1003 and operation 1004. In a case where j reaches xmax in operation 1004, the image processing apparatus 501 increments i by 1 (operation 1005). In a case where i<n, the image processing apparatus 501 repeats the processing of operation 1001 to operation 1005. In a case where i reaches n in operation 1005, the image processing apparatus 501 ends the processing.

Figure 11:
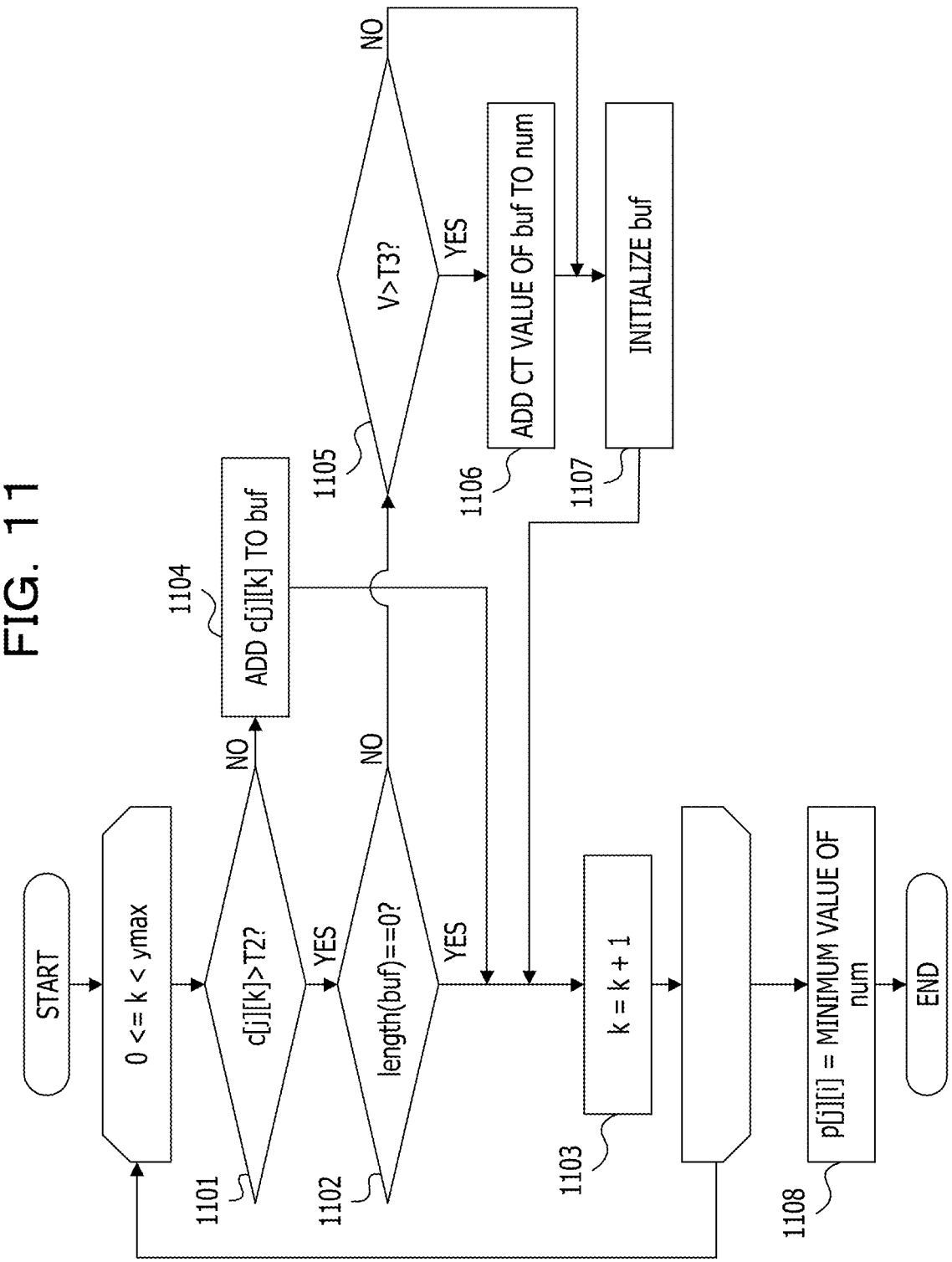
FIG. 11 is a flowchart of pixel value calculation processing.

FIG. 11 is a flowchart illustrating an example of pixel value calculation processing in operation 1003 in FIG. 10. In the pixel value calculation processing in FIG. 11, an array buf and an array num are used. The array buf is a variable-length array that stores CT values of one partial pixel column corresponding to the lung field region or the region W. The array num is a variable-length array that stores the CT values of one or a plurality of partial pixel columns corresponding to the lung field region. The initial values of the lengths of the array buf and the array num are 0.

First, the identification unit 513 sets 0 for a control variable k indicating the y coordinate of the processing target CT image, and compares the CT value c[j][k] of the pixel at the position (j,k) in the processing target CT image, with the threshold T2 (operation 1101).

In a case where c [j][k]>T2 (operation 1101, YES), the identification unit 513 checks the length length(buf) of the array buf (operation 1102). In a case where length(buf)=0 (operation 1102, YES), the identification unit 513 increments k by 1 (operation 1103), and in a case where k<ymax, the processing in operation 1101 and subsequent operations are repeated.

In a case where c[j][k] T2 (operation 1101, NO), the identification unit 513 adds c[j][k] to the array buf (operation 1104). Thus, the CT value of the pixel corresponding to the lung field region or the region W is added to the array buf, and length(buf) is incremented by 1. The identification unit 513 performs the processing in operation 1103 and subsequent operations.

In a case where length(buf)>0 (operation 1102, NO), the identification unit 513 obtains the statistical value V of one or more CT values included in the array buf, and compares the statistical value V with the threshold T3 (operation 1105). In a case where V>T3 (operation 1105, YES), the identification unit 513 adds one or more CT values included in the array buf to the array num (operation 1106). Thus, the CT values of the partial pixel column corresponding to the lung field region are added to the array num.

Next, the identification unit 513 initializes the array buf (operation 1107). Thus, length(buf)=0. The identification unit 513 performs the processing in operation 1103 and subsequent operations. In a case where V T3 (operation 1105, NO), the identification unit 513 skips the processing of operation 1106, and performs the processing in operation 1107 and subsequent operations. Thus, the CT values of the partial pixel column corresponding to the region W are ignored.

In a case where k reaches ymax in operation 1103, the generation unit 514 obtains the minimum value of one or more CT values included in the array num, and sets the minimum value for p[j][i] (operation 1108). In a case where a CT value is not stored in the array num, the generation unit 514 sets a predetermined value equal to or greater than the threshold T2 for p[j][i].

The image processing apparatus 501 may generate a coronal image of the hollow organ instead of the coronal image 526 of the lung field, by using the coronal image generation processing in FIG. 10. In a case where a coronal image of the hollow organ is generated, the determination condition "V>T3?" in operation 1105 in FIG. 11 is changed to "V<T3?".

Thus, in a case where V<T3, the identification unit 513 adds one or more CT values included in the array buf to the array num (operation 1106), and in a case where V T3, the identification unit 513 skips the processing of operation 1106. Thus, the CT values of one or a plurality of partial pixel columns corresponding to the region W are stored in the array num.

The image processing apparatus 501 may also identify a part corresponding to a region in the medical image by performing the same image processing on the medical image other than the CT image. A magnetic resonance imaging (MRI) image, an ultrasonic image, or the like is used as the medical image other than the CT image.

The configurations of the image processing apparatus 301 in FIG. 3 and the image processing apparatus 501 in FIG. 5 are merely examples, and some components may be omitted or changed according to the use or conditions of the image processing apparatus. For example, in the image processing apparatus 501 in FIG. 5, the acquisition unit 512 may be omitted in a case where the learning CT image 521 and the CT image 525 are stored in advance in the storage unit 511. In a case where the extraction model 524 is generated by another image processing apparatus and is stored in the storage unit 511, the learning unit 515 may be omitted. In a case where it is not necessary to determine the upper end and the lower end of the lung field, the determination unit 516 may be omitted.

The flowcharts in FIG. 4 and FIGS. 8 to 11 are merely examples, and a part of the processing may be omitted or changed according to the configuration or conditions of the image processing apparatus. For example, in the image processing in FIG. 8, the processing in operation 801 may be omitted in a case where the learning CT image 521 is stored in advance in the storage unit 511. In a case where the extraction model 524 is generated by another image processing apparatus and is stored in the storage unit 511, the image processing in FIG. 8 may be omitted.

In the image processing in FIG. 9, in a case where the CT image 525 is stored in advance in the storage unit 511, the processing of operation 901 may be omitted. In a case where the upper end and the lower end of the lung field are determined from the coronal image 526 without using the extraction model 524, the processing in operation 903 may be omitted. In a case where it is not necessary to determine the upper end and the lower end of the lung field, the processing in operation 903 and operation 904 may be omitted.

The CT images illustrated in FIGS. 1, 2, and 7 are merely examples, and the CT image varies depending on the patient and the body part. The coronal images illustrated in FIGS. 1, 2, and 6 are merely examples, and the coronal image varies depending on the CT images.

Figure 12:
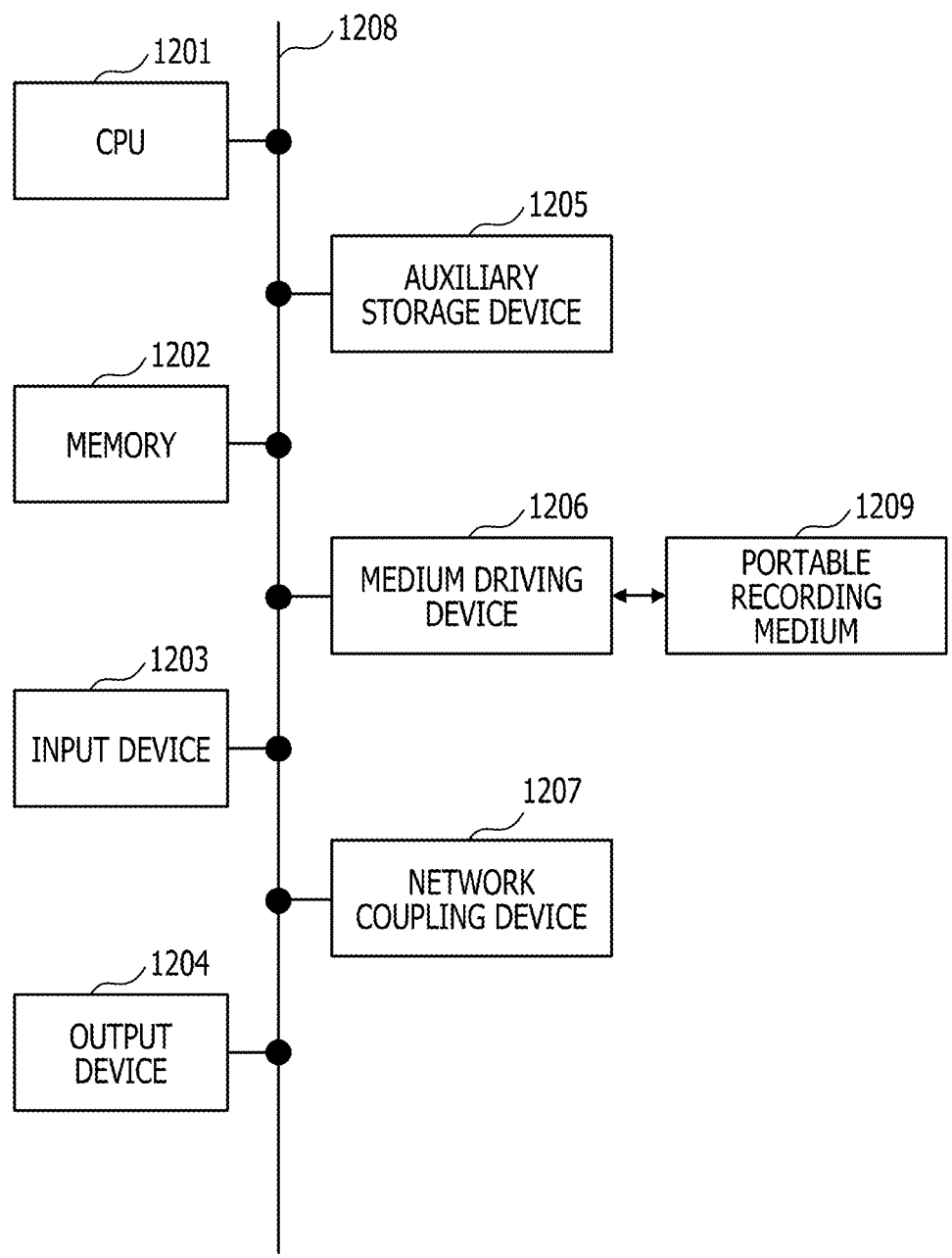
FIG. 12 is a hardware configuration diagram of an information processing apparatus.

FIG. 12 illustrates a hardware configuration example of an information processing apparatus (computer) used as the image processing apparatus 301 in FIG. 3 and the image processing apparatus 501 in FIG. 5. The information processing apparatus in FIG. 12 includes a central processing unit (CPU) 1201, a memory 1202, an input device 1203, an output device 1204, an auxiliary storage device 1205, a medium driving device 1206, and a network coupling device 1207. These components are pieces of hardware, and are coupled to each other by a bus 1208. The CT apparatus 502 in FIG. 5 may be coupled to the network coupling device 1207.

The memory 1202 is, for example, a semiconductor memory such as a read-only memory (ROM), a random-access memory (RAM), or a flash memory, and stores a program and data to be used in processing. The memory 1202 may be used as the storage unit 311 in FIG. 3 or the storage unit 511 in FIG. 5.

The CPU 1201 (processor) executes a program using, for example, the memory 1202 to operate as the identification unit 312 in FIG. 3. The CPU 1201 executes a program using the memory 1202 to also operate as acquisition unit 512, the identification unit 513, the generation unit 514, the learning unit 515, and the determination unit 516 in FIG. 5.

The input device 1203 is, for example, a keyboard, a pointing device, or the like, and is used for an operator or a user to input instructions or information. The output device 1204 is, for example, a display device, a printer, a speaker, or the like, and is used for outputting inquiries or instructions to an operator or a user and outputting a processing result. The processing result may be the region information 527 or the position information 528.

The auxiliary storage device 1205 is, for example, a magnetic disk device, an optical disk device, a magneto-optical disk device, a tape device, or the like. The auxiliary storage device 1205 may be a hard disk drive or a flash memory. The information processing apparatus stores a program and data in the auxiliary storage device 1205, and may use the program and data by loading them into the memory 1202. The auxiliary storage device 1205 may be used as the storage unit 311 in FIG. 3 or the storage unit 511 in FIG. 5.

The medium driving device 1206 drives a portable recording medium 1209, and accesses the contents recorded therein. The portable recording medium 1209 is a memory device, a flexible disk, an optical disk, a magneto-optical disk, or the like. The portable recording medium 1209 may be a compact disc read-only memory (CD-ROM), a digital versatile disc (DVD), a Universal Serial Bus (USB) memory, or the like. The operator or the user may store a program and data in the portable recording medium 1209, and may use the program and data by loading them into the memory 1202.

A computer-readable recording medium in which a program and data to be used in processing are stored as described above is a physical (non-transitory) recording medium such as the memory 1202, the auxiliary storage device 1205, or the portable recording medium 1209.

The network coupling device 1207 is a communication interface circuit that is coupled to a communication network such as a local area network (LAN) or a wide area network (WAN) and that performs data conversion involved in communication. The information processing apparatus may receive a program and data from external devices via the network coupling device 1207, and may use the program and data by loading them into the memory 1202.

The information processing apparatus may also receive the CT image 525 and a processing request from a user terminal via the network coupling device 1207, and transmit the region information 527 or the position information 528 to the user terminal.

The information processing apparatus does not necessarily include all of the components in FIG. 12, and part of the components may be omitted depending on the use or conditions. For example, in a case where the information processing apparatus receives a processing request from a user terminal, the input device 1203 and the output device 1204 may be omitted. In a case where the portable recording medium 1209 or the communication network is not used, the medium driving device 1206 or the network coupling device 1207 may be omitted.

While the embodiment of the disclosure and advantages thereof have been described in detail, those skilled in the art may make various changes, additions, and omissions without departing from the scope of the disclosure, which is set forth in the appended claims.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium having stored an image processing program that causes a computer to execute a process, the process comprising:
   extracting a plurality of consecutive pixels corresponding to a first part or a second part of a body, from a pixel column in a predetermined direction of an image of the body;
   obtaining a statistical value of pixel values of the plurality of consecutive pixels; and
   identifying a part corresponding to the plurality of consecutive pixels, among the first part or the second part, based on the statistical value, wherein the first part is a lung field and the second part is a part other than the lung field, and wherein the process further includes:
   by using a computed tomography image of each of a plurality of slices of the body as the image of the body and using each of a plurality of pixel columns in the computed tomography image as the pixel column in the predetermined direction, identifying a position of a pixel column including pixels corresponding to the lung field among the plurality of pixel columns by identifying the part corresponding to the plurality of consecutive pixels,
   generating a coronal image of the lung field, based on the position of the pixel column including the pixels corresponding to the lung field, wherein the position of the pixel column being identified in the computed tomography image of each of the plurality of slices, and
   identifying an upper end and a lower end of the lung field by using the coronal image,
   wherein the identifying of the part includes identifying the part corresponding to the plurality of consecutive pixels, based on a comparison result between the statistical value and a first threshold as a Hounsfield unit (HU).

2. The non-transitory computer-readable recording medium according to claim 1,
   wherein the extracting of the plurality of consecutive pixels includes extracting the plurality of consecutive pixels based on a comparison result between a second threshold and a pixel value of each of a plurality of pixels included in the pixel column in the predetermined direction.

3. An image processing apparatus comprising:
   a memory configured to store an image of a body; and
   a processor coupled to the memory and configured to:
   extract a plurality of consecutive pixels corresponding to a first part or a second part of the body, from a pixel column in a predetermined direction of the image of the body;
   obtain a statistical value of pixel values of the plurality of consecutive pixels; and
   identify a part corresponding to the plurality of consecutive pixels, among the first part or the second part, based on the statistical value;
   wherein the first part is a lung field and the second part is a part other than the lung field, and
   wherein the processor is further configured to:
   by using a computed tomography image of each of a plurality of slices of the body as the image of the body and using each of a plurality of pixel columns in the computed tomography image as the pixel column in the predetermined direction, identify a position of a pixel column including pixels corresponding to the lung field among the plurality of pixel columns by identifying the part corresponding to the plurality of consecutive pixels,
   generate a coronal image of the lung field, based on the position of the pixel column including the pixels corresponding to the lung field, wherein the position of the pixel column being identified in the computed tomography image of each of the plurality of slices, and
   identify an upper end and a lower end of the lung field by using the coronal image,
   wherein the processor identifies the part corresponding to the plurality of consecutive pixels, based on a comparison result between the statistical value and a first threshold as a Hounsfield unit (HU).

4. The image processing apparatus according to claim 3,
   wherein the processor extracts the plurality of consecutive pixels based on a comparison result between a second threshold and a pixel value of each of a plurality of pixels included in the pixel column in the predetermined direction.

5. An image processing method that causes a computer to execute a process, the process comprising:
   extracting a plurality of consecutive pixels corresponding to a first part or a second part of a body, from a pixel column in a predetermined direction of an image of the body;
   obtaining a statistical value of pixel values of the plurality of consecutive pixels; and
   identifying a part corresponding to the plurality of consecutive pixels, among the first part or the second part, based on the statistical value;
   wherein the first part is a lung field and the second part is a part other than the lung field, and
   wherein the process further includes:
   by using a computed tomography image of each of a plurality of slices of the body as the image of the body and using each of a plurality of pixel columns in the computed tomography image as the pixel column in the predetermined direction, identifying a position of a pixel column including pixels corresponding to the lung field among the plurality of pixel columns by identifying the part corresponding to the plurality of consecutive pixels, generating a coronal image of the lung field, based on the position of the pixel column including the pixels corresponding to the lung field, wherein the position of the pixel column being identified in the computed tomography image of each of the plurality of slices, and identifying an upper end and a lower end of the lung field by using the coronal image wherein the identifying of the part includes identifying the part corresponding to the plurality of consecutive pixels, based on a comparison result between the statistical value and a first threshold as a Hounsfield unit (HU).

6. The image processing method according to claim 5, wherein the extracting of the plurality of consecutive pixels includes extracting the plurality of consecutive pixels based on a comparison result between a second threshold and a pixel value of each of a plurality of pixels included in the pixel column in the predetermined direction.

* * * * *